(12) United States Patent
Tsotsoros et al.

(10) Patent No.: US 8,197,799 B2
(45) Date of Patent: *Jun. 12, 2012

(54) HAIR CARE FORMULATIONS

(75) Inventors: Rhonda F. Tsotsoros, Ramsey, NJ (US);
Fatima Ehsan, Greensboro, NC (US);
John Jennings, Yonkers, NY (US);
Harald Chrobaczek, Augsburg (DE)

(73) Assignee: BASF SE, Ludwigshafen (DE)

(*) Notice: Subject to any disclaimer, the term of this patent is extended or adjusted under 35 U.S.C. 154(b) by 1607 days.

This patent is subject to a terminal disclaimer.

(21) Appl. No.: 11/249,797

(22) Filed: Oct. 13, 2005

(65) Prior Publication Data

US 2006/0115447 A1     Jun. 1, 2006

Related U.S. Application Data

(60) Provisional application No. 60/619,127, filed on Oct. 15, 2004, provisional application No. 60/701,097, filed on Jul. 20, 2005.

(51) Int. Cl.
*A61Q 5/02* (2006.01)
*A61Q 5/04* (2006.01)
*A61Q 5/06* (2006.01)
*A61Q 5/08* (2006.01)
*A61Q 5/10* (2006.01)
*A61Q 5/12* (2006.01)

(52) U.S. Cl. .................. 424/70.12; 424/70.1; 424/70.2; 424/70.6

(58) Field of Classification Search .......... None
See application file for complete search history.

(56) References Cited

U.S. PATENT DOCUMENTS

| | | | | |
|---|---|---|---|---|
| 3,890,269 | A | 6/1975 | Martin | 260/46.5 |
| 4,247,330 | A * | 1/1981 | Sanders, Jr. | 106/3 |
| 4,563,347 | A | 1/1986 | Starch | 424/70 |
| 4,586,518 | A | 5/1986 | Cornwall et al. | 132/7 |
| 4,606,933 | A | 8/1986 | Griswold et al. | 427/54.1 |
| 4,620,878 | A | 11/1986 | Gee | 6/287.15 |
| 4,762,887 | A | 8/1988 | Griswold et al. | 522/99 |
| 5,132,443 | A | 7/1992 | Traver et al. | 556/425 |
| 5,275,755 | A | 1/1994 | Sebag et al. | 252/174.15 |
| 5,302,322 | A | 4/1994 | Birtwistle | 252/547 |
| 5,308,551 | A | 5/1994 | Beauquey et al. | 252/548 |
| 5,599,483 | A | 2/1997 | Mizushima et al. | 510/119 |
| 5,968,492 | A | 10/1999 | Noguchi et al. | 424/70.1 |
| 6,090,885 | A | 7/2000 | Kuo et al. | 524/838 |
| 6,123,934 | A | 9/2000 | Koyama et al. | 424/70.11 |
| 6,353,073 | B1 | 3/2002 | Biggs et al. | 528/14 |
| 2001/0008917 | A1 | 7/2001 | Craig et al. | 524/588 |
| 2002/0034483 | A1 | 3/2002 | Avery et al. | 424/70.1 |
| 2003/0224954 | A1 * | 12/2003 | Wells et al. | 510/119 |
| 2005/0063934 | A1 * | 3/2005 | Baker et al. | 424/70.122 |

FOREIGN PATENT DOCUMENTS

WO 2004/052963  6/2004
WO 2004/069899  8/2004

OTHER PUBLICATIONS

English language abstract for DE 196 52 524 printed from espacenet.com website on Jan. 13, 2006.
English Abstract AN-2000-492767[44] for JP 2000-154318 (Jun. 2000).

* cited by examiner

*Primary Examiner* — Jyothsna Venkat
(74) *Attorney, Agent, or Firm* — Shiela A. Loggins; Tyler A. Stevenson

(57) ABSTRACT

This invention relates to hair conditioning formulations comprising at least one aminofunctional polyorganosiloxane. Furthermore, the invention relates to the use of these formulations for the treatment of keratin-containing fibers, preferably human hair.

9 Claims, No Drawings

HAIR CARE FORMULATIONS

This application claims the benefit of Application Nos. 60/619,127, filed Oct. 15, 2004 and 60/701,097, filed Jul. 20, 2005.

This invention relates to hair care formulations, particularly hair conditioning formulations, comprising at least one aminofunctional polyorganosiloxane. Furthermore, the invention relates to the use of these formulations for the treatment of keratin-containing fibers, preferably human hair.

It is known to treat fiber materials, in particular flat textile structures with polyorganosiloxanes. The fiber materials can be provided with advantageous properties such as, for example a pleasant, soft touch. Polyorganosiloxanes that contain quaternary groups having a nitrogen atom, and the use of such polyorganosiloxanes for the treatment of textile fiber materials are known as well, for example from DE-A 196 52 524.

It is also known to use aminofunctional polyorganosiloxanes in personal conditioning applications, for example in the treatment of hair. See for example U.S. Pat. Nos. 4,563,347, 4,586,518, 4,620,878, 5,132,443 and 6,090,885, the disclosures of which are incorporated by reference in their entirety.

The use of these polysiloxanes still show some disadvantages in view of the stability properties, buildup properties, or the use may interfere with other hair processes such as perming or dyeing.

The aim of the present invention was to find a hair conditioning formulation which does not show these disadvantages.

The present invention relates to hair conditioning formulations comprising at least one aminofunctional polyorganosiloxane of formula (I)

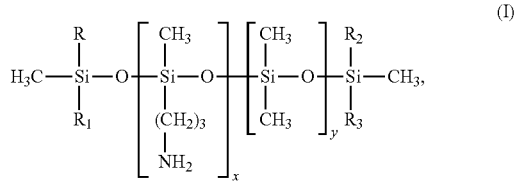

wherein
R, $R_1$, $R_2$ and $R_3$ independently from each other are $CH_3$, OH or $OC_1$-$C_4$alkyl,
x is an integer from 1 to 200,
y is an integer from 1 to 500,
and the molecular weight of the aminofunctional polysiloxane is from 5000 to 50000 D.

Preferably the ratio x:y is from 1:10 to 1:100, more preferably from −1:20 to 1:80.

Preferably the molecular weight is 5000 to 40000 D, more preferably from 8000 to 30000 D, especially preferably from 10000 to 25000 D. The molecular weight can be determined by known methods, such as gel permeation chromatography (GPC).

Preferably R, $R_1$, $R_2$ and $R_3$ independently from each other are $CH_3$, OH or $OC_1$-$C_2$alkyl.

Polyorganosiloxanes typically contain significant amounts of volatile components, for example residual solvents and cyclic siloxane oligomers such as $D_3$ (hexamethylcyclotrisiloxane), $D_4$ (octamethylcyclotetrasiloxane) & $D_5$ (decamethylcyclopentasiloxane) as artifacts of their manufacture. Preferably the aminofunctional polyorganosiloxane of formula (I) contains 0.1% by weight or less of volatile solvent and hexamethylcyclotrisiloxane, less than 0.5% by weight of octamethylcyclotetrasiloxane and less than 1.0% by weight of cyclopentasiloxane, based on the total amount of the polyorganosiloxane of formula (I). More preferably the aminofunctional polyorganosiloxane of formula (I) contains less than 1.5% by weight in total of residual solvent, hexamethylcyclotrisiloxane, octamethylcyclotetrasiloxane and decamethylcyclopentasiloxane based on the total amount of the polyorganosiloxane of formula (I). Methods of reducing the amount of volatile components in polyorganosiloxanes are well known to those of ordinary skill in the art.

The hair conditioning formulations preferably contain from 0.05% to 10% by weight (wt-%) of the polyorganosiloxane of formula (I); more preferably they contain from 0.1 wt-% to 8 wt-%, especially preferably from 0.1 wt-% to 5 wt-% of it, based on the total amount of the hair conditioning formulation.

A further embodiment of the present invention relates to a hair conditioning formulation comprising
0.05 wt-% to 10 wt %, based on the total weight of the hair conditioning formulation, of at least one aminofunctional polyorganosiloxane of formula (I)

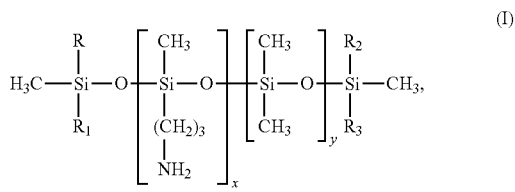

wherein
R, $R_1$, $R_2$ and $R_3$ independently from each other are $CH_3$, OH or $OC_1$-$C_4$alkyl,
x is an integer from 1 to 200,
y is an integer from 1 to 500,
and the molecular weight of the aminofunctional polysiloxane is from 5000 to 50000 D.

A preferred embodiment of the present invention relates to a hair conditioning formulation comprising
0.1 wt-% to 8 wt %, based on the total weight of the hair conditioning formulation, of at least one aminofunctional polyorganosiloxane of formula (I)

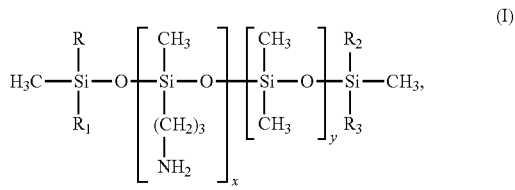

wherein
R, $R_1$, $R_2$ and $R_3$ independently from each other are $CH_3$, OH or $OC_1$-$C_2$alkyl,
x is an integer from 1 to 200,
y is an integer from 1 to 500,
and the molecular weight of the aminofunctional polysiloxane is from 5000 to 40000 D and wherein the ratio of x:y is 1:20 to 1:80.

The polysiloxanes of formula (I) are not known (i.e. concretely disclosed) in U.S. Pat. No. 4,586,518 or U.S. Pat. No. 4,563,347, but they can be produced by analogy to the processes that can be found therein. Methods of reducing the amount of volatile components in polysiloxanes are well known to those of ordinary skill in the art.

Since the diluent only serves to dilute the silicone polymer to allow uniform application of appropriately small quantities, any diluent that is physiologically acceptable for contact with the human body when used in a cosmetic composition may be used. For example, the silicone polymer can be dissolved in organic solvents such as alcohols, for example ethanol and isopropanol, or polyols such as propylene glycol. Mixtures thereof with water may also be employed. Alternatively, the silicone polymer is used in the form of an aqueous dispersion or emulsion.

Highly stable aqueous dispersions can be obtained by adding one or several dispersing agents. Suitable as dispersants are surface-active compounds known to those skilled in the field of silicone emulsions. Nonionic products such as fatty alcohol ethoxylates, fatty acid ethoxylates, or ethoxylated fatty amines, or cationically-active dispersants such as, for example quaternized ammonium salts may be mentioned here in particular. The amount of dispersant(s) is in the range of, for example from 2% to 10% by weight based on the total dispersion. The dispersions can be produced by generally known methods employed for dispersing polysiloxanes.

The polyorganosiloxane compositions as defined above are useful in cosmetic formulations for hair treatment, for example hair washes in the form of shampoos, hair conditioners, such as also thermal protection conditioners, hair-conditioning products, for example pretreatment products, hair tonics, hair styling creams and gels, pomades, hair rinses, deep conditioning treatments, intensive hair conditioning treatments, hair setting products, for example waving agents for permanents (hot wave, mild wave, cold wave), hair straightening products, liquid hair fixatives, hair foams, hair sprays, temporary, semi-temporary or permanent hair dyes, products containing self-oxidizing dyes, or natural hair dyes such as henna or camomile. Depending on the specific hair treating application, the composition of this invention may be formulated by conventional means into aerosol, pump spray, spritz, lotion, cream, gel, or mousse type compositions for easy application to hair.

The formulations of this invention impart excellent, long lasting conditioning without build-up and do not interfere with other hair processes such as perming and dyeing.

The term "hair" as used in the present invention includes treated and untreated human hair, animal hair, and any type of hair-like fiber that needs gloss, reduced fly-away and ease of combing. Treated hair includes hair that is chemically changed and/or damaged by permanents and/or dyes.

Creams are usually spreadable in the temperature range from room to skin temperature, whereas cream rinses, lotions or milks tend to be pourable.

Gels are semisolid systems in which the so-called gel former forms a three-dimensional network in which a liquid is immobilized. Clear to opaque hydrogels consist primarily of water, water-soluble substances and thickeners or gel formers.

In addition to the essential ingredients specified above, the formulation of this invention may comprise further ingredients (additives) which are conventional and/or beneficial. Examples of such other ingredients (additives) are thickeners and stabilizers, e.g., sodium alginate, gum arabic, polyoxyethylene, guar gum, hydroxypropyl guar gum, cellulose derivatives such as methylcellulose, methylhydroxypropylcellulose, hydroxypropylcellulose, polypropylhy-droxyethylcellulose, starch and starch derivatives such as hydroxyethylamylose and starch amylose, and locust bean gum;

perfumes;

hair root nutrients, such as such as amino acids and sugars. Examples of suitable amino acids include arginine, cysteine, glutamine, glutamic acid, isoleucine, leucine, methionine, serine and valine, and/or precursors and derivatives thereof. The amino acids may be added singly, in mixtures, or in the form of peptides, e.g. di- and tripeptides. The amino acids may also be added in the form of a protein hydrolysate, such as a keratin or collagen hydrolysate. Suitable sugars are glucose, dextrose and fructose. These may be added singly or in the form of, e.g. fruit extracts. A particularly preferred combination of natural hair root nutrients for inclusion in compositions of the invention is isoleucine and glucose. A particularly preferred amino acid nutrient is arginine;

polyols, such as such as glycerine and polypropylene glycol;

chelating agents, such as EDTA;

foam boosters;

antifoam agents;

antioxidants;

antimicrobials;

sunscreens;

bactericides;

solvents, e.g., ethanol SDA40;

organic resins, e.g., polyquaternium 11;

emulsifiers, e.g., ceteareth 20, steareth 20, stearyl alcohol, and polysorbate 20;

emollient oils, e.g., dimethicone and cyclomethicone;

preservatives, e.g., methyl paraben, methylisothiazolinone;

opacifiers;

sequestering agents;

pH adjusting agents, e.g., citric acid;

dyes;

specialty additives, such as re-fatting agents (e.g., isopropyl myristate and palmitate, cetyl alcohol, propylene glycol), pearlescent agents (e.g., ethylene glycol distearate), dandruff control agents (e.g., zinc pyrithione);

further polysiloxanes, such as polydiorganosiloxanes, in particular polydimethylsiloxanes which have the CTFA designation dimethicone. Also suitable for use in compositions of the invention are polydimethyl siloxanes having hydroxyl end groups, which have the CTFA designation dimethiconol. It is preferred if the silicone oil also comprises a functionalized silicone. Suitable functionalized silicones include, for example, amino-, carboxy-, betaine-, quaternary ammonium-, carbohydrate-, hydroxy- and alkoxy-substituted silicones. Preferably, the functionalized silicone contains multiple substitutions. For the avoidance of doubt, as regards hydroxyl-substituted silicones, a polydimethylsiloxane merely having hydroxyl end groups (which have the CTFA designation dimethiconol) is not considered a functionalized silicone within the present invention. However, a polydimethylsiloxane having hydroxyl substitutions along the polymer chain is considered a functionalized silicone. Suitable amino functionalized silicones are described in EP 455,185 (Helene Curtis) and include trimethylsilylamodimethicone as depicted below, and are sufficiently water insoluble so as to be useful in compositions of the invention:

$Si(CH_3)_3-O-[Si(CH_3)_2-O-]_x-[Si(CH_3)(R-NH-CH_2CH_2NH_2)O-]_y-Si(CH_3)_3$ wherein x+y is a number from about 50 to about 500, and the weight percent amine functionality is in the range of from about 0.03% to about 8% by weight of the molecule, and wherein R is an alkylene group having from 2 to 5 carbon atoms. As expressed here, the weight percent amine functionality is measured by titrating a sample of the amino-functionalized silicone against alcoholic hydrochloric acid to the bromocresol green end point. The weight percent amine is calculated using a molecular weight of 45 (corresponding to $CH_3$—$CH_2$—$NH_2$). Suitably, the weight percent amine functionality measured and calculated in this way is in the range from 0.03% to 8%, preferably from 0.5% to 4%. An example of a commercially available amino-functionalized silicone useful in the silicone component of the composition of the invention is DC-8566 available from Dow Corning (INCI name: dimethyl, methyl(aminoethylaminoisobutyl)siloxane). This has a weight percent amine functionality of about 1.4%. Examples of suitable amino functional silicones include: polysiloxanes having the CTFA designation "amodimethicone". Specific examples of amino functional silicones suitable for use in the invention are the aminosilicone oils DC-8220, DC-8166, DC-8466, and DC-8950-114 (all ex Dow Corning), and GE 1149-75, (ex General Electric Silicones). Suitable quaternary silicone polymers are described in EP-A-0 530 974. A preferred quaternary silicone polymer is K3474, ex Goldschmidt. Another preferred functional silicone for use as a component in the hydrophobic conditioning oil is an alkoxy-substituted silicone. Such molecules are known as silicone copolyols and have one or more polyethylene oxide or polypropylene oxide groups bonded to the silicone polymer backbone, optionally through an alkyl linking group. A non-limiting example of a type of silicone copolyol useful in compositions of the invention has a molecular structure according to the formula depicted below:

$Si(CH_3)_3[O—Si(CH_3)(A)]_p—[O—Si(CH_3)(B)]_q—O—Si(CH_3)_3$. In this formula, A is an alkylene chain with from 1 to 22 carbon atoms, preferably 4 to 18, more preferably 10 to 16. B is a group with the structure: —(R)—(EO)$_r$(PO)S—OH wherein R is a linking group, preferably an alkylene group with 1 to 3 carbon atoms. Preferably R is —$(CH_2)_2$—. The mean values of r and s are 5 or more, preferably 10 or more, more preferably 15 or more. It is preferred if the mean values of r and s are 100 or less. In the formula, the value of p is suitably 10 or more, preferably 20 or more, more preferably 50 or more and most preferably 100 or more. The value of q is suitably from 1 to 20 wherein the ratio p/q is preferably 10 or more, more preferably 20 or more. The value of p+q is a number from 11 to 500, preferably from 50 to 300.

Suitable silicone copolyols have an HLB of 10 or less, preferably 7 or less, more preferably 4 or less. A suitable silicone copolyol material is DC5200, known as Lauryl PEG/PPG-18/18 methicone (INCI name), available from Dow Corning.

It is preferred to use a combination of functional and non-functional silicones as the hydrophobic silicone conditioning oil. Preferably the silicones are blended into common droplets prior to incorporation into compositions according to the invention.

The viscosity of the hydrophobic silicone conditioning oil, measured in isolation from the rest of the composition (i.e. not the viscosity of any pre-formed emulsion, but of the hydrophobic conditioning oil itself) is typically from 350 to 200,000,000 $mm^2sec^{-1}$ at 25° C. Preferably the viscosity is at least 5,000 $mm^2sec^{-1}$ at 25° C., more preferably at least 10,000 $mm^2 sec^{-1}$. Preferably the viscosity does not exceed 20,000,000 $mm^2sec^{-1}$, more preferably 10,000,000 $mm^2sec^{-1}$, most preferably 5,000,000 $mm^2sec^{-1}$.

Suitable methods for measuring the kinematic viscosity of silicone oils are known to those skilled in the art, e.g. capillary viscometers. For high viscosity silicones, a constant stress rheometer can also be used to measure dynamic viscosity, which is related to kinematic viscosity by the density of the silicone. The viscosity should be measured at low shear rates, typically less than 10 s, such that the silicone exhibits Newtonian behavior (i.e. viscosity independent of shear rate);

conventional hair conditioning agents such as waxes, oils, stearalkonium chloride, dicetyidimonium chloride, stearamidopropyl dimethylamine, and other quaternary organic compounds; and an additive that reduces static electricity build-up and flyaway. Such an additive is preferably a quaternary amine.

Each of these ingredients will be present in an amount effective to accomplish its purpose. Generally these optional ingredients are included individually at a level of up to 5% by weight of the total hair conditioning formulation.

The hair treating formulation of this invention can be applied, for example, in the form of a shampoo; rinsing products to be applied after shampooing, before or after tinting or bleaching, and before or after permanent waving or straightening; products for setting or brushing; conditioning compositions; restoring compositions; and compositions for permanent-waved hair. The hair treating formulation of this invention is preferably applied in rinsing products to be applied after shampooing, tinting or bleaching, and after permanent waving or straightening; or in products for setting or brushing; conditioning compositions; restoring compositions; and compositions for conditioning permanent-waved hair.

In one embodiment of the invention the hair treating formulation is a shampoo, in which case the composition contains a cleansing surfactant in addition to about 0.1 to 10 parts by weight of the polyorganosiloxane polymer and the aqueous diluent. The concentration of cleansing surfactant can range from about 8 to 60 parts by weight of total shampoo formulation.

Cleansing surfactants selected from the group consisting of anionic surfactants, nonionic surfactants, and amphoteric surfactants are well known for use in shampoo formulations. Typical cleansing surfactants include the anionic surfactants such as the sodium, ammonium, or triethanolamine salts of lauryl sulfate and lauryl ether sulfate; the nonionic surfactants such as fatty acid alkanolamides like lauric acid diethanolamide; and the amphoteric surfactants such as N-cocamidopropyl dimethyl glycine. Generally, the anionic surfactants, especially the sodium, ammonium, and triethanolamine salts of lauryl sulfate, are preferred since they provide richer, denser foams than other types of cleansing surfactants at comparable concentrations.

Additionally the shampoo contains from 0 up to 15 parts of so-called secondary surfactants such as decyl glucoside or sodium cocoamphoacetate, from 0 up to 2 parts of a polymeric conditioning agent such as polyquaternium-7, from 0 up to 4 parts of a thickener such as cocamide MEA, magnesium aluminum silicate or an acrylate or acrylamide copolymer, from 0 up to 3 parts of super fatting agents such as PPG-5 Ceteth 20 and Oleath 20, from 0 up to 3 parts of auxiliary conditioning agents such as Panthenol and hydrolyzed wheat protein, from 0 up to 2 parts of pearlizing/opacifying agents such as glycol distearate and ethylene glycol stearate, from 0 up to 5 parts of other active ingredients such as zinc pyrithione (48% soln.) and conventional amounts of other adjuvants such as stabilizers, pH and viscosity adjusters, colorants and perfumes, to name just a few, each by weight of the total shampoo composition. The inventive shampoo compositions contain at least one of the above-mentioned additional ingredients.

In another embodiment of the invention, the hair treating composition of this invention is a conditioning product for application to hair after shampooing. The hair is typically rinsed in running water after treatment with the conditioning composition. Conditioners facilitate combing out hair and impart softness and suppleness to the hair. Conditioning compositions may also contain other components such as thickeners and auxiliary conditioning compounds. Auxiliary conditioning agents may be used to provide further improved conditioning benefits such as antistatic characteristics. Auxiliary conditioning agents useful in the composition of this invention include organic cationic compounds and polymers such as stearyidimethylbenzylammonium chloride or bromide, lauryl-trimethylammonium chloride or bromide, dodecyldimethylhydroxyethylammonium chloride or bromide, dimethyldistearylammonium chloride or bromide and dimethyldi-laurylammonium chloride or bromide, quaternary nitrogen derivatives of cellulose ethers, and homopolymers and copolymers of dimethyldiallylammonium chloride such as the SALCONDITIONING® range of hair conditioning polymers available from Ciba Specialty Chemicals Corporation, High Point N.C., homopolymers or copolymers derived from acrylic acid or methacrylic acid containing cationic nitrogen functional groups attached to the polymer via ester or amide linkages, copolymers of vinylpyrrolidone and acrylic acid esters with quaternary nitrogen functionality and other quaternary ammonium compounds which are known for use in hair conditioning formulations. They are used in conventional amounts to attain the desired effects.

When the hair treating composition of this invention is a conditioning product for application to hair after shampooing, it contains, in addition to about 0.1 to 10 parts by weight of the above-described polysiloxane polymer and the diluent, from 1 up to about 4 parts of refatting agents such as fatty alcohols, for example cetyl or stearyl alcohol and waxes or lanolin derivatives. Additionally it may contain from 0.2 up to 3.0 parts of secondary conditioning agents such as natural oils and silicones, from 0 up to 6 parts of emulsifiers such as nonionic surfactants and liquid dispersion polymers such as SALCONDITIONING® SC92, SC95, SC96 polymers available from Ciba Specialty Chemicals Corporation, High Point N.C., and conventional amounts of other adjuvants such as proteins, polymeric resins and gums, preservatives, pH and viscosity adjusters, colorants and per-fumes, to name just a few, each by weight of the total composition.

Additionally a leave-in conditioner advantageously contains from 0.5 up to 7 parts of primary conditioning agents, for example cationic surfactants like dicetyldimonium chloride and cetrimonium chloride.

Aerosol mousse formulations typically contain 8 to 15 parts by weight of gaseous propellants, and gel formulations typically contain 0.25 to 1 parts by weight of a gelling agent/thickener.

Alcoholic lotions and tonics are systems in which oils are dissolved in alcohol permitting a thin, uniform film of oils to remain on the hair after the alcohol has evaporated. When the hair treating composition of this invention is a lotion or tonic it contains, in addition to about 0.1 to 10 parts by weight of the above-described polysiloxane polymer, about 40 to 95 parts by weight of SD 40 alcohol (190 proof). Advantageously it also contains about 0.5 to 4 parts by weight of a fixative polymer, such as a PVP/VA copolymer, about 0.1 to 0.5 parts by weight of a plasticizer such as a dimethicone copolymer, about 0.1 to 2 parts by weight of conditioning agents/emollients such as Panthenol and propylene glycol, and conventional amounts of other adjuvants such as preservatives, perfumes and neutralizers and, to name just a few, each by weight of the total composition.

When the hair treating composition of this invention is a pump spray liquid it contains, in addition to about 0.1 to 10 parts by weight of the above-described polysiloxane polymer, about 55 to 95 parts by weight of SD 40 alcohol (200 proof) and 0 to 40 parts by weight of water. Typically it also contains about 2 to 16 parts by weight of a hair fixative resin.

Advantageously it may contain ingredients such as 0 to 1 parts by weight of DL-Panthenol, vitamin E acetate and herbal extracts, and conventional amounts of other adjuvants such as neutralizing agents like aminomethyl propanol, sodium hydroxide and ammonium hydroxide, and perfumes, to name just a few, each by weight of the total composition.

The present invention also includes a method of treating hair, which comprises applying to the surface of the hair an effective amount of the composition of this invention. The composition may be applied in any suitable manner, such as by massaging the composition throughout the hair by hand, by dipping the hair into the composition, by brushing or combing the composition throughout the hair or by spraying.

After the composition is applied, the hair may or may not be rinsed, depending on whether the composition applied is a rinsable or non-rinsable composition.

Generally, the amount of hair treating composition that is applied is that amount which is effective to thoroughly coat the hair. The amount required will vary with the quantity and type of hair of each individual. Appropriate amounts for any individual's hair are readily determined by one or several trial applications. The length of time in which the conditioner should be left on the hair will also vary according to hair type. Generally, if the hair treating composition is a rinsable conditioner, it is left on the hair for a period of from at least about 30 seconds to about 2 minutes.

A further embodiment of the present invention is a formulation for a conditioning shampoo comprising
a) 0.05 to 10 wt-%, preferably 0.1 to 8 wt-% and more preferably 0.1 to 5 wt-%, based on the total weight of the formulation, of at least one polysiloxane of formula (I),
b) 5 to 30 wt-%, preferably 10 to 20 wt-% based on the total weight of the formulation, of at least one non-ionic, and/or an anionic and/or an amphoteric surfactant,
c) 0.2 to 5 wt-% of at least one thickener,
d) 0-5 wt-% of at least one further additive, and
e) water up to 100 wt-%.

A preferred embodiment of the present invention is a formulation for a conditioning shampoo comprising
a) 0.1 to 8 wt-%, preferably 0.1 to 5 wt-%, based on the total weight of the formulation, of at least one polysiloxane of formula (I)

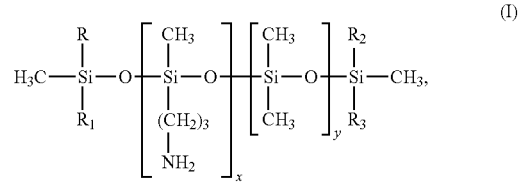

wherein
R, $R_1$, $R_2$ and $R_3$ independently from each other are $CH_3$, OH or $OC_1$-$C_4$alkyl,
x is an integer from 1 to 200,
y is an integer from 1 to 500,
and the molecular weight of the aminofunctional polysiloxane is from 5000 to 40000 D and wherein the ratio of x:y is 1:20 to 1:80,
b) 10 to 20 wt-% based on the total weight of the formulation, of at least one non-ionic, and/or an anionic and/or an amphoteric surfactant,
c) 0.2 to 5 wt-% of at least one thickener,
d) 0-5 wt-% of at least one further additive, and
e) water up to 100 wt-%.

Preferably these compositions have a pH between 5.0 and 7.0.

Suitable examples of nonionic surfactants are alkoxylated alcohols, alkyl polyglycosides, alkoxylated sorbitan esters, alkoxylated monoethanolamides, alkoxylated fatty acids and alkoxylated glycerides. The alkoxylates could contain a hydrophobic alkyl or acyl group with 8-22 carbon atoms, and the alkyleneoxy groups could be ethyleneoxy or propyleneoxy groups and the number of these groups could be between 2-15, preferably 3-10.

Suitable examples of anionic surfactants are alkyl sulfates, alkylaryl sulfates, alkyl ether sulfates, alkyl and alkylaryl sulfonates, olefin sulfonates, secondary alkyl sulfonates, sodium acyl isethionates, monoalkyl sulfosuccinates, acyl-N-alkyltaurates and protein-fatty acids condensates.

Suitable examples of amphoteric surfactants are N-alkyl betaines, N-alkyl glycinates, N-alkyl aminopropionates, N-alkyl iminodipropionates or alkyl imidazolines. Especially suitable examples are cocoamidopropyl betaine, cocodimethyl betaine, cocoamphocarboxy glycinate, cocoamphocarboxy propionates and coco or oleyl polyamino carboxylates.

The thickener can be an inorganic salt, such as sodium chloride or ammonium chloride; a cellulose ether, e.g. ethyl hydroxyethyl cellulose; or a synthetic polymer, such as polyacrylic acid derivatives, polyalkylene glycols and di- or polyurethanes of polyethoxylated compounds.

In addition the composition may also contain a skin compatible pH-adjustment agent, perfume oil, preservatives, opacifiers, pearlescent agents, dyes, humectants and refatting agents. The 2-in-1 shampoos most often also contain silicones, such as dimethicones, or silicone derivatives, e.g. quaternium 80, as additional conditioning agents. The conditioning shampoo and the body wash may also contain emollients and active ingredients such as vitamins.

A suitable formulation for a hair conditioner contains
a) 0.05 to 10 wt-%, preferably 0.1 to 8 wt-% and more preferably 0.1 to 5 wt-%, based on the total weight of the formulation, of at least one polysiloxane of formula (I),
b) 0.5 to 5 wt-%, preferably 1 to 4 wt-%, based on the total weight of the formulation, of at least one long chain fatty alcohol,
c) at least one skin compatible acid in an amount sufficient to obtain a pH between 2.5 to 5.5, preferably 3-5 and more preferably around 3.5,
d) 0-5 wt-%, based on the total weight of the formulation, of at least one further additive, and
e) water up to 100 wt-%.

A preferred formulation for a hair conditioner contains
a) 0.1 to 8 wt-%, preferably 0.1 to 5 wt-%, based on the total weight of the formulation, of at least one polysiloxane of formula (I)

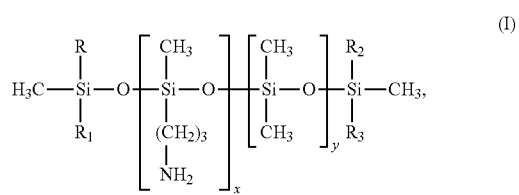

wherein
R, $R_1$, $R_2$ and $R_3$ independently from each other are $CH_3$, OH or $OC_1$-$C_4$alkyl,
x is an integer from 1 to 200,
y is an integer from 1 to 500,
and the molecular weight of the aminofunctional polysiloxane is from 5000 to 40000 D and wherein the ratio of x:y is 1:20 to 1:80,
b) 1 to 4 wt-%, based on the total weight of the formulation, of at least one long chain fatty alcohol,
c) at least one skin compatible acid in an amount sufficient to obtain a pH between 3-5, preferably around 3.5,
d) 0-5 wt-%, based on the total weight of the formulation, of at least one further additive, and
e) water up to 100 wt-%.

The long chain fatty alcohol could contain 12 to 22 carbon atoms, preferably 16-18 carbon atoms.

The acid can for example be citric, lactic, tartaric, adipic or phosphoric acid or their salts.

The composition can also contain a thickener, for example a cellulose-based thickener such as ethyl hydroxyethyl cellulose.

Another optional ingredient is a quaternary ammonium surfactant, such as mono- di- or trialkyl quats and mono- di- and triacyl ester quats. The quaternary compounds may also be ethoxylated.

Other ingredients that may be added are emulsifiers; oils such as silicon oils, triglycerides or mineral oil; dyes, humectants, polyols, vitamins and hydrophobic esters containing either a long chain fatty acid or a long chain fatty alcohol.

The following examples describe certain embodiments of this invention, but the invention is not limited thereto. It should be understood that numerous changes to the disclosed embodiments could be made in accordance with the disclosure herein without departing from the spirit or scope of the invention. These examples are therefore not meant to limit the scope of the invention. Rather, the scope of the invention is to be determined only by the appended claims and their equivalents. In these examples all parts given are by weight unless otherwise indicated.

EXAMPLES

For all the Examples, a sample of compound A according to formula (I)

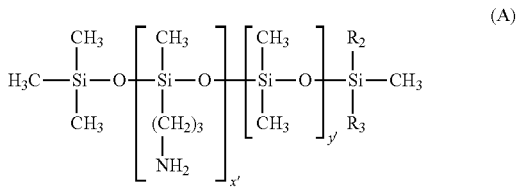

is used which contains 0.1% by weight or less of volatile solvent and hexamethylcyclotrisiloxane, 0.2% by weight of octamethylcyclotetrasiloxane and 0.1% by weight of decamethylcyclopentasiloxane (by HPGC), based on the total amount of the polyorganosiloxane of formula (I), obtained by heating a stirred sample of a commercial grade of an amodimethicone of formula (1) to about 100° C., gradually reducing the vacuum to below 1 torr and holding for several hours. The molecular weight is about 15'000 D-20'000 D and the ratio of x':y' is about 1:30. The formulations are prepared by combining the listed ingredients by mixing methods well known in the cosmetic art

Example 1

Deep Conditioner

| | Ingredients | Amount [wt-%] |
|---|---|---|
| 1 | Water | to 100 |
| 2 | Polyquaterium-32 and Mineral Oil | 2.00 |
| 3 | Hydrogenated Polyisobutene | 4.00 |
| 4 | Glyceryl Monostearate and PEG 100 Stearate | 1.50 |
| 5 | Glycerin | 2.00 |
| 6 | Compound (A) | 3.00 |
| 7 | Polysorbate-20 | 1.50 |
| 8 | Cyclopentasiloxane (and) Cyclohexasiloxane | 2.00 |
| 9 | Dimethicone (and) Dimethiconol | 2.50 |
| 10 | Sunflower Seed Oil | 0.50 |
| 11 | Fragrance | 0.20 |
| 12 | Mixture of Diazolidinyl Urea and Iodoprpynyl Butylcarbamate | 1.00 |

Procedure:

Mix fiirst two ingredients with moderate mixing, heat to 75-80° C.

In a separate vessel mix ingredients 3-10 with moderate mixing, heat to 75-80° C.

Combine the mixtures together with moderate mixing.

When both are fully mixed and uniform, begin cooling.

At 55° C. add 11 and 12; continue cooling and mixing until 25° C.

Example 2

Thermal Protection Conditioner (Leave-In)

| | Ingredients | Amount [wt-%] |
|---|---|---|
| 1 | Water | to 100 |
| 2 | Sodium Acrylates Copolymer (and) Mineral Oil (and) PPG-1 Trideceth-6 | 1.00 |
| 3 | Compound (A) | 0.30 |
| 4 | Polysorbate-20 | 0.30 |
| 5 | Cyclopentasiloxane (and) Cyclohexasiloxane | 0.25 |
| 6 | PEG-12 Dimethicone | 0.40 |
| 7 | Fragrance | 0.20 |
| 8 | Mixture of Diazolidinyl Urea and Iodopropynyl Butylcarbamate | 0.75 |

Procedure:

Heat ingredient 1 to 60° C. first and add ingredient 2 with moderate mixing. When fully hydrated and uniform, add additional ingredients one at a time ensuring they are fully mixed and uniform before next addition.

Mix until uniform and cool the mixture to 25° C.

Example 3

Color Retention/Protection Conditioner

| | Ingredients | Amount [wt-%] |
|---|---|---|
| 1 | Water | to 100 |
| 2 | Polyquaterium-32 and Mineral Oil | 2.00 |
| 3 | Glyceryl Monostearate and PEG 100 Stearate | 3.50 |
| 4 | Polysorbate 20 | 1.00 |
| 5 | Compound (A) | 2.00 |
| 6 | Cyclopentasiloxane (and ) Cyclohexasiloxane | 2.00 |
| 7 | Sodium Benzotriazolyl Butylphenol Sulfonate, Buteth-3, Tirbutyl Citrate | 1.00 |
| 8 | Cetyl Alcohol | 2.50 |
| 9 | Fragrance | 0.20 |
| 10 | Mixture of Diazolidinyl Urea (and) Iodopropynyl Butylcarbamate | 1.00 |

Procedure:

Mix first two ingredients with moderate mixing; heat to 75-80° C.

In a separate vessel mix ingredients 3-8 with moderate mixing; heat to 75-80° C.

When both are fully mixed and uniform add together with moderate mixing.

Begin cooling. At 55° C. add 9 and 10; continue cooling and mixing until 25° C.

Example 4

Styling Pomade

| | Ingredients | Amount [wt-%] |
|---|---|---|
| 1 | Water | to 100 |
| 2 | VP/Methacrylamide/Vinyl Imidazole Copolymer | 6.00 |
| 3 | Propylene Glycol | 3.00 |
| 4 | Dimethicone Copolyol Meadowfoamate | 1.00 |
| 5 | Mixture of Diazolidinyl Urea (and) Iodopropynyl Butylcarbamate | 0.50 |
| 6 | PPG-Ceteth-20 | 0.50 |
| 7 | Compound (A) | 0.40 |
| 8 | Fragrance | 0.20 |
| 9 | Polyquaternium-37 (and) Propylene Glycol Dicaprylate/Dicaprate (and) PPG-1 Trideceth-6 | 2.00 |

Procedure:

Mix first two ingredients with moderate mixing.

When fully hydrated and uniform, add additional ingredients one at a time; ensure each is fully mixed and uniform before the next addition.

Mix until uniform.

Example 5

Long Straight Hair Conditioner

|   | Ingredients | Amount [wt-%] |
|---|---|---|
| 1 | Water | to 100 |
| 2 | Polyquaterium-32 and Mineral Oil | 1.00 |
| 3 | Cetyl Alcohol | 2.00 |
| 4 | Glyceryl Monostearate PEG-100 Stearate | 4.00 |
| 5 | Polysorbate 20 | 1.25 |
| 6 | Compound (A) | 2.50 |
| 7 | Cyclopentasiloxane (and) Cyclohexasiloxane | 1.00 |
| 8 | Phenyl Trimethicone | 1.50 |
| 9 | Fragrance | 0.20 |
| 10 | Mixture of Diazolidinyl Urea and Iodopropynyl Butylcarbamate | 1.00 |

Procedure:

Mix first two ingredients with moderate mixing, heat to 75-80° C.

In separate vessel mix ingredients 3-8 with moderate mixing; heat to 75-80° C.

When both are fully mixed and uniform add together with moderate mixing.

Begin cooling. At 55° C. add 9 and 10; continue cooling and mixing until 25° C.

Example 6

Rinse-Out Conditioner

|   | Ingredients | Amount [wt-%] |
|---|---|---|
| 1 | Water | to 100 |
| 2 | Polyquaternium-32 and Mineral Oil | 0.50 |
| 3 | Cetearyl Alcohol | 5.00 |
| 4 | Glyceryl Monostearate and PEG-100 Stearate | 3.00 |
| 5 | Polysorbate 20 | 0.50 |
| 6 | Compound (A) | 2.22 |
| 7 | Cyclopentasiloxane (and) Cyclohexasiloxane | 2.00 |
| 8 | Dimethicone (and) Dimethiconol | 0.50 |
| 9 | Sunflower Seed Oil | 0.50 |
| 10 | Avocado Oil | 0.50 |
| 11 | Fragrance | 0.20 |
| 12 | Mixture of Phenoxyethanol, Methyl Paraben, Butyl Paraben, Propyl Paraben and Isobutyl Paraben | 1.00 |

Procedure:

Mix first two ingredients with moderate mixing; heat to 75-80° C.

Premix ingredients 5, 6 and 8 together in a separate vessel. Add ingredients 3, 4, 7, 9 and 10 one at a time to the same vessel with moderate mixing; heat to 75-80° C.

When both are fully mixed and uniform add together with moderate mixing.

Begin cooling. At 55° C. add 10; continue cooling and mixing until 25° C.

Example 7

Rinse-Out Conditioner

|   | Ingredients | Amount [wt-%] |
|---|---|---|
| 1 | Water | 92.52 |
| 2 | Disodium EDTA | 0.10 |
| 3 | Propylene Glycol | 3.00 |
| 4 | Aminopropyl Dimethicone | 2.22 |
| 5 | Phenoxyethanol, Methyl Paraben, Butyl Paraban, Propyl Paraben, Isobutyl Paraben | 1.00 |
| 6 | Propylene Glycol and water and Synphytum Officinale Leaf Extract | 0.10 |
| 7 | Sodium Benzotriazolyl Butylphenol Sulfonate and Buteth-3 and Tributyl Citrate | 0.15 |
| 8 | FD & C Yellow 5 | 0.01 |
| 9 | Sodium Acrylates Copolymer and Mineral Oil and Tridecth-6 | 0.90 |

Procedure:

Mix ingredients 1-7 with moderate mixing.

When fully mixed and uniform add ingredient 8.

Mix until fully hydrated and uniform.

Example 8

Glossy Serum

|   | Ingredients | Amount [wt-%] |
|---|---|---|
| 1 | Cyclomethicone and Dimethicone Crosspolymer | 20.00 |
| 2 | Cyclopentasiloxane and Dimethicone | 12.00 |
| 3 | Phenyl Trimethicone | 64.69 |
| 4 | Meadowfoam Seed Oil & Shea Butter Extract | 1.00 |
| 5 | Ethylhexyl Methoxycinnamate | 1.00 |
| 6 | Compound (A) | 1.11 |
| 7 | Perfume | 0.20 |

Add ingredients one at a time, ensuring each is fully mixed and uniform before next addition.

Mix until uniform.

Example 9

Smoothing Gloss Serum

|   | Ingredients | Amount [wt-%] |
|---|---|---|
| 1 | Cyclomethicone | 53.69 |
| 2 | Cyclopentasiloxane (and) Dimethicone | 15.00 |
| 3 | Phenyl Trimethicone | 28.00 |
| 4 | Meadowfoam Seed Oil and Shea Butter Extract | 1.00 |
| 5 | Compound (A) | 1.11 |
| 6 | Ethylhexyl Methoxycinnamate | 1.00 |
| 7 | Fragrance Oil | 0.20 |

Add ingredients one at a time, ensuring each is fully mixed and uniform before next addition.

Mix until uniform.

What is claimed is:

1. A hair conditioning formulation comprising at least one aminofunctional polyorganosiloxane of formula (I)

$$H_3C-\underset{\underset{R_1}{|}}{\overset{\overset{R}{|}}{Si}}-O-\left[\underset{\underset{(CH_2)_3}{|}}{\overset{\overset{CH_3}{|}}{Si}}-O\right]_x\left[\underset{\underset{CH_3}{|}}{\overset{\overset{CH_3}{|}}{Si}}-O\right]_y\underset{\underset{R_3}{|}}{\overset{\overset{R_2}{|}}{Si}}-CH_3,$$
$$\text{(with } NH_2 \text{ on the } (CH_2)_3 \text{ group)}$$

wherein
R, $R_1$, $R_2$ and $R_3$ independently from each other are $CH_3$, OH or $OC_1$-$C_4$alkyl,
wherein the ratio x:y is from 1:20 to 1:80,
which contains 0.1% by weight or less of hexamethylcyclotrisiloxane, less than 0.5% by weight of octamethylcyclotetrasiloxane and less than 1.0% by weight of decamethylcyclopentasiloxane, and
a diluent that is physiologically acceptable for contact with the human body when used in a cosmetic composition, wherein the conditioning formulation is selected from the group consisting of shampoo, hair conditioner, hair pretreatment product, hair tonic, hair styling cream, hair styling gel, pomade, hair rinse, deep conditioning treatment, intensive hair conditioning treatment, hair setting product, hair straightening product, liquid hair fixative, hair foam, hair spray, temporary, semi-temporary, permanent hair dye, a product containing self-oxidizing dyes and a product containing natural hair dyes.

2. A hair conditioning formulation according to claim 1, comprising from 0.05% to 10% by weight of the at least one aminofunctional polyorganosiloxane of formula (I), based on the total amount of the hair conditioning formulation.

3. A hair conditioning formulation according to claim 2, comprising from 0.1% to 8% by weight of the at least one aminofunctional polyorganosiloxane of formula (I), based on the total amount of the hair conditioning formulation.

4. A hair conditioning formulation according to claim 2, comprising from 0.1% to 5% by weight of the at least one aminofunctional polyorganosiloxane of formula (I), based on the total amount of the hair conditioning formulation.

5. A conditioning shampoo comprising
a) 0.05 to 10 wt-%, based on the total weight of the formulation, of at least one aminofunctional polyorganopolysiloxane of formula (I), $$H_3C-\underset{\underset{R_1}{|}}{\overset{\overset{R}{|}}{Si}}-O-\left[\underset{\underset{(CH_2)_3}{|}}{\overset{\overset{CH_3}{|}}{Si}}-O\right]_x\left[\underset{\underset{CH_3}{|}}{\overset{\overset{CH_3}{|}}{Si}}-O\right]_y\underset{\underset{R_3}{|}}{\overset{\overset{R_2}{|}}{Si}}-CH_3,$$
$$\text{(with } NH_2 \text{ on the } (CH_2)_3 \text{ group)}$$

wherein a ratio x:y is from 1:20 to 1:80,
R, $R_1$, $R_2$ and $R_3$ independently from each other are $CH_3$, OH or $OC_1$-$C_4$alkyl,
which contains 0.1% by weight or less of hexamethylcyclotrisiloxane, less than 0.5% by weight of octamethylcyclotetrasiloxane and less than 1.0% by weight of decamethylcyclopentasiloxane
b) 5 to 30 wt-%, based on the total weight of the formulation, of at least one non-ionic, and/or an anionic and/or an amphoteric surfactant,
c) 0.2 to 5 wt-% of at least one thickener,
d) 0-5 wt-% of at least one further additive, and
e) water up to 100 wt-%.

6. A conditioning shampoo according to claim 5 comprising
a) 0.1 to 8 wt-%, based on the total weight of the formulation, of at least one aminofunctional polyorganosiloxane of formula (I)
b) 10 to 20 wt-% based on the total weight of the formulation, of at least one non-ionic, and/or an anionic and/or an amphoteric surfactant.

7. A hair conditioner comprising
a) 0.05 to 10 wt-%, based on the total weight of the formulation, of at least one aminofunctional polyorganosiloxane of formula (I), $$H_3C-\underset{\underset{R_1}{|}}{\overset{\overset{R}{|}}{Si}}-O-\left[\underset{\underset{(CH_2)_3}{|}}{\overset{\overset{CH_3}{|}}{Si}}-O\right]_x\left[\underset{\underset{CH_3}{|}}{\overset{\overset{CH_3}{|}}{Si}}-O\right]_y\underset{\underset{R_3}{|}}{\overset{\overset{R_2}{|}}{Si}}-CH_3,$$
$$\text{(with } NH_2 \text{ on the } (CH_2)_3 \text{ group)}$$

wherein x:y is a ratio from 1:20 to 1:80,
R, $R_1$, $R_2$ and $R_3$ independently from each other are $CH_3$, OH or $OC_1$-$C_4$alkyl,
which contains 0.1% by weight or less of hexamethylcyclotrisiloxane, less than 0.5% by weight of octamethylcyclotetrasiloxane and less than 1.0% by weight of decamethylcyclopentasiloxane
b) 0.5 to 5 wt-%, based on the total weight of the formulation, of at least one long chain fatty alcohol,
c) at least one skin compatible acid in an amount sufficient to obtain a pH between 2.5 and 5.5,
d) 0 to 5 wt-%, based on the total weight of the formulation, of at least one further additive, and
e) water up to 100 wt-%.

8. A hair conditioner according to claim 7 comprising
a) 0.1 to 8 wt-%, based on the total weight of the formulation, of at least one aminofunctional polyorganosiloxane of formula (I)
b) 1 to 4 wt-%, based on the total weight of the formulation, of at least one long chain fatty alcohol,
c) at least one skin compatible acid in an amount sufficient to obtain a pH between 3-5.

9. A method for the treatment of hair comprising the step contacting the hair with a hair conditioning formulation according to claim 1.